(12) United States Patent
Georgi et al.

(10) Patent No.: US 8,307,704 B2
(45) Date of Patent: Nov. 13, 2012

(54) APPARATUS AND METHODS FOR GAS VOLUME RETAINED CORING

(75) Inventors: Daniel T. Georgi, Houston, TX (US); Larry M. Hall, Kingwood, TX (US); Baoyan Li, Spring, TX (US)

(73) Assignee: Baker Hughes Incorporated, Houston, TX (US)

( * ) Notice: Subject to any disclaimer, the term of this patent is extended or adjusted under 35 U.S.C. 154(b) by 406 days.

(21) Appl. No.: 12/641,692

(22) Filed: Dec. 18, 2009

(65) Prior Publication Data

US 2010/0161229 A1    Jun. 24, 2010

Related U.S. Application Data

(60) Provisional application No. 61/139,944, filed on Dec. 22, 2008.

(51) Int. Cl.
*E21B 49/02* (2006.01)
(52) U.S. Cl. .................................... 73/152.07
(58) Field of Classification Search ............... 73/152.07
See application file for complete search history.

(56) References Cited

U.S. PATENT DOCUMENTS

| | | | |
|---|---|---|---|
| 4,256,192 A | | 3/1981 | Aumann |
| 4,371,045 A | * | 2/1983 | McGuire et al. ............... 175/17 |
| 4,466,495 A | | 8/1984 | Jageler |
| 5,265,462 A | * | 11/1993 | Blauch et al. .................. 73/38 |
| 5,741,959 A | * | 4/1998 | Garcia et al. ................ 73/19.05 |
| 6,097,310 A | | 8/2000 | Harrell et al. |
| 2002/0043620 A1 | | 4/2002 | Tchakarov et al. |
| 2008/0123470 A1 | | 5/2008 | Cooper et al. |
| 2008/0162056 A1 | * | 7/2008 | Greaves ........................ 702/24 |

FOREIGN PATENT DOCUMENTS

| | | |
|---|---|---|
| CA | 1198983 | 1/1986 |
| WO | WO2004017708 A3 | 3/2004 |

OTHER PUBLICATIONS

Web document from internet archive of web page www.corpro-group.com/gas.html, "Core Gas Services," May 8, 2006, 1 page.*
Corpro Corebarrels, Corpro, http://www.corpro-group.com/gas.htm, Dec. 10, 2008.
Total S.A. Coring Guide, V1 Oct. 2005, pp. 25-26.

* cited by examiner

*Primary Examiner* — John Fitzgerald
(74) *Attorney, Agent, or Firm* — Mossman, Kumar & Tyler, P.C.

(57) ABSTRACT

An apparatus for use in a wellbore may include a tool having a first section configured to receive a core and a second section configured to collect a gas escaping from the core. The apparatus may also include a sensor associated to provide signals relating to a property of gas. In one aspect, the second section may be removable and may be pressurized. The apparatus may also include a recorder that records data representative of the signals received from the sensor. The recorder may record data while the tool is retrieved from the wellbore. A method for estimating a parameter of interest of a formation includes retrieving a core from the formation, collecting a gas escaping from the core as the core is retrieved to the surface, and measuring at least one property of gas while the core is retrieved to the surface.

20 Claims, 2 Drawing Sheets

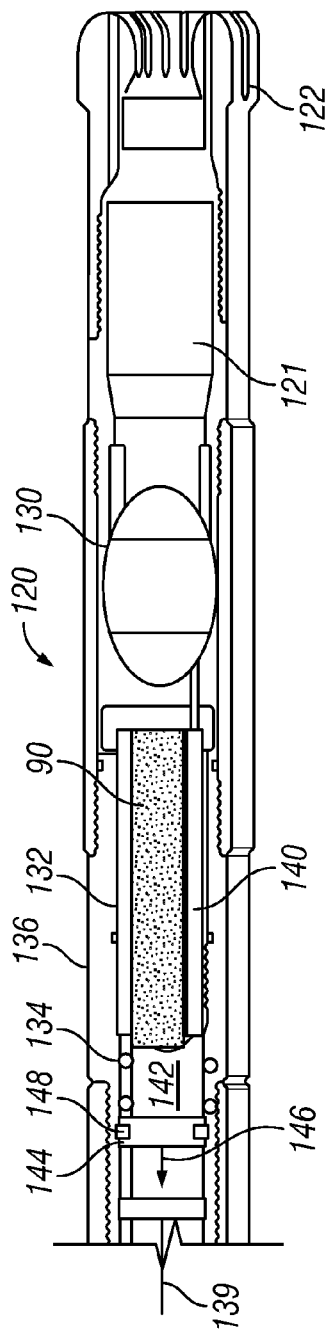
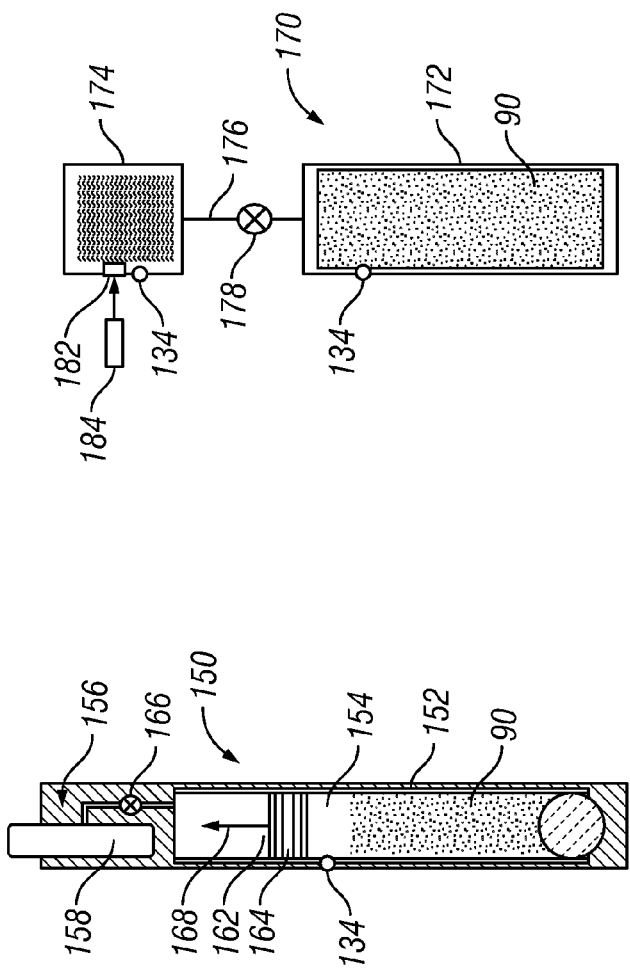
FIG. 1B
FIG. 3
FIG. 2

APPARATUS AND METHODS FOR GAS VOLUME RETAINED CORING

CROSS-REFERENCE TO RELATED APPLICATIONS

This application claims priority from the U.S. Provisional Patent Application Ser. No. 61/139,944 filed Dec. 22, 2008.

BACKGROUND OF THE DISCLOSURE

1. Field of the Disclosure

The disclosure herein relates generally to obtaining cores from a formation and estimating one or more properties of interest downhole.

2. Description of the Related Art

Hydrocarbons, such as oil and gas, often reside in porous subterranean geologic formations. Often, it can be advantageous to use a coring tool to obtain representative samples of rock taken from a formation of interest. Such rock samples obtained are generally referred to as "core samples." Analysis and study of core samples enables engineers and geologists to assess important formation parameters such as the reservoir storage capacity (porosity), the flow potential (permeability) of the rock that makes up the formation, the composition of the recoverable hydrocarbons or minerals that reside in the formation, and the irreducible water saturation level of the rock. For instance, in both tight and shale gas plays, information as to the amount of gas may be useful in the subsequent design and implementation of a well completion program that enables production of selected formations and zones that are determined to be economically attractive based on the data obtained from the core sample.

The present disclosure addresses the need to obtain core samples that may be utilized to estimate one or more parameters of interest relating to a subsurface formation of interest.

SUMMARY

The present disclosure, in one aspect, provides systems, apparatus and methods for recovering cores cut from a subterranean formation as well as gas escaping from such cores. In one aspect, an apparatus for such a use may include a barrel having a first section for receiving the core and a second section for collecting gas escaping from the core. The apparatus may also include one or more sensors to provide signals relating to a property of interest relating to the escaping gas. The pressure in either or both of the sections may be controlled by a pressure application device. Also, the second section may be removable from the first section and may also be substantially gas tight. Illustrative sensors include a pressure sensor, a temperature sensor, and sensor to estimate the gas volume, such as an acoustic sensor. The apparatus may also include a recorder that records data representative of the signals received from the sensor(s). The recorder may record data as the barrel is retrieved from a selected depth in the wellbore to a surface location.

In aspects, the present disclosure also provides a method for estimating a parameter of interest relating to a formation. The method may include retrieving a core from the formation; collecting a gas escaping from the core as the core is retrieved to the surface; and measuring at least one parameter of interest relating to the escaping gas while the core is retrieved to the surface. The method may also include controlling a pressure applied to either or both of the core and the gas escaping from the core. In embodiments, the method may include containing the escaped gas in a container that is removable or detachable from the container for the core. In aspects, the parameters of interest that are measured include pressure, temperature, and a volume occupied by the escaping gas. The method may further include measuring the parameters as the escaped gas and core are retrieved to the surface. The method may also include estimating a gas saturation, a permeability, and/or porosity of a formation using one or more of the measured parameters.

Aspects of the apparatus and methods disclosed herein have been summarized broadly to acquaint the reader with the subject matter of the disclosure and it is not intended to be used to limit the scope of the concepts, methods or embodiments related thereto of claims that may be made pursuant to this disclosure. An abstract is provided to satisfy certain regulatory requirements and is not to be used to limit the scope of the concepts, methods and embodiments related thereto to the claims that may be made pursuant to this disclosure.

BRIEF DESCRIPTION OF THE DRAWINGS

For detailed understanding of the present disclosure, references should be made to the following detailed description of the apparatus and methods for retrieving cores and estimating one or more properties or characteristics of the core and formation, taken in conjunction with the accompanying drawings, in which like elements have generally been given like numerals, wherein:

FIG. 1 (comprising FIGS. 1A and 1B) is a schematic diagram of a drilling system for coring and for estimating one or more parameters of interest of a core and/or an escaped gas, wherein FIG. 1A shows an exemplary surface apparatus and FIG. 1B shows an exemplary downhole apparatus of the coring system;

FIG. 2 is a schematic diagram of a portion of a coring assembly that utilizes a pressure application device to apply a selected pressure to a sample according to one embodiment of the disclosure; and FIG. 3 is a schematic diagram of a portion of a coring assembly that includes a removable storage chamber for storing an escaped gas according to one embodiment of the present disclosure.

DETAILED DESCRIPTION OF THE EMBODIMENTS

Figure 1A:
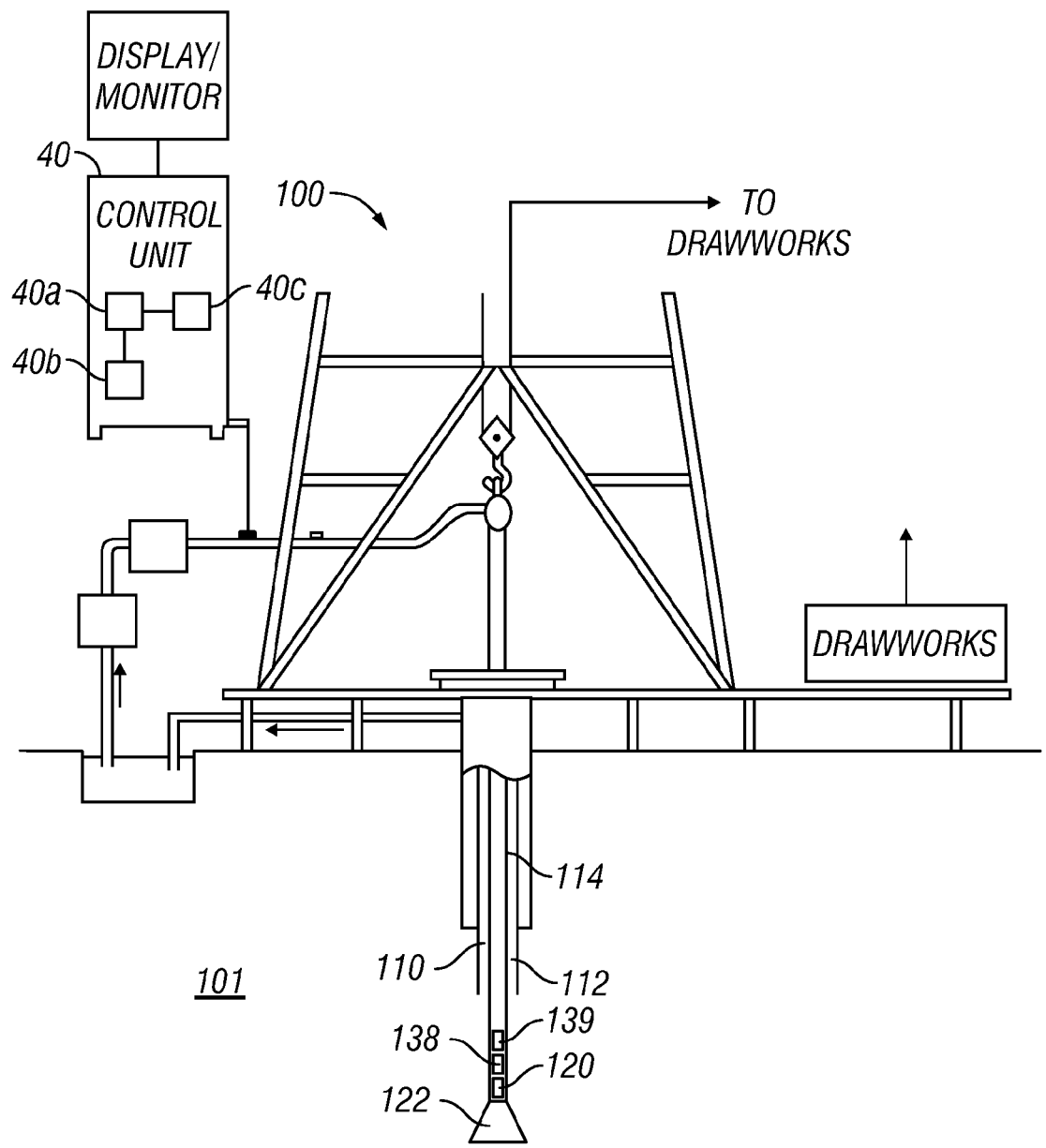

The present disclosure relates to devices and methods for obtaining a sample from subterranean formations. The term "sample" includes a core, any fluids in the core, and/or any gases that escape from the core. The present disclosure is susceptible to embodiments of different forms. There are shown in the drawings, and herein will be described in detail, specific embodiments of the present disclosure with the understanding that the present disclosure is to be considered an exemplification of the principles of the disclosure, and is not intended to limit the disclosure to that illustrated and described herein. Indeed, as will become apparent, the teachings of the present disclosure can be utilized for a variety of well tools and in all phases of well construction and production. Accordingly, the embodiments discussed below are merely illustrative of the applications of the present disclosure.

Embodiments of the present disclosure may be utilized during well construction to obtain geological and geophysical data associated with reservoir models for evaluating the economic value of a given formation. In aspects, illustrative devices collect or retain the gas that escapes from a formation core sample as the core is brought from the sub-surface to the surface. This gas escapes because the confining pressure is reduced from the bottom hole pressure to atmospheric pressure during the core retrieval process. By collecting, quantifying and analyzing this escaped gas, estimates may be made as to the total gas saturation of the formation from which the formation sample had been taken. The collected gas may also be used to obtain addition information as to the geophysical properties, petrophysical properties, chemical properties or other characteristics, such as energy content, of the formation.

Referring initially to FIG. 1 (comprising FIG. 1A and FIG. 1B) there is schematically illustrated an exemplary sample retrieval system 100 that may be utilized for obtaining coring samples, estimating one or more properties of the core and/or estimating formation parameters according to one aspect of the disclosure. FIG. 1 shows a wellbore 110 being drilled with a drill string 112 in a formation 101. The drill string 112, in one aspect, includes a tubular member 114 and a coring assembly 120 at its bottom end. The tubular member 114 is typically made up by connecting drill pipe sections. A drill bit 122 (also referred to herein as the "coring bit") is attached to the bottom end of the coring assembly 120. In some embodiments, the coring assembly 120 may be a drilling assembly that is configured to form the wellbore 110. An exemplary drilling device suitable for both drilling and coring includes the COREDRILL™ coring system available from Baker Hughes Incorporated. Such a configuration may utilize a mud motor, a steering assembly, thrusters, and other components that may be associated with a drilling assembly. In other embodiments, the coring assembly 120 may be specially configured to retrieve only core samples. The system 100 may include a surface control unit 40 may transmit to and receive signals from the coring assembly 120. The signals may include control signals for controlling operation of the coring assembly 120 and/or data signals representative of measurements made by any number of sensors associated with the coring assembly 120. The surface control unit 40 may be a computer-based system that may include a processor 40a, a memory module 40b for storing data, computer programs, models and algorithms accessible to the processor 40a, and a recorder 40c for recording data and other peripherals. It should be understood that the present teachings are not limited to any particular system configuration. For instance, embodiments of the present disclosure may be utilized with non-rigid conveyance devices such as wirelines instead of rigid conveyance devices such as drill pipe or coiled tubing.

Referring now to FIG. 1B, there is shown in further detail the coring assembly 120 that can retrieve a core sample, store a core sample, collect a gas escaping the core sample, and/or measure one or more parameters associated with the core 90 and/or gas escaping from the core 90. In one embodiment, the coring assembly 120 includes a sealing member 130, such as a ball valve, a barrel 132, and one or more sensors 134. In one arrangement, the sensors 134 may transmit signals directly to the surface. In other arrangements, the coring assembly 120 may include a downhole controller or control unit 138 (FIG. 1A) that receives the signals from the sensors 134. The controller 138 (FIG. 1A), in one aspect, may include a processor, such as microprocessor, one or more data storage devices (or memory devices) and other circuitry configured to control data collection, data processing and/or data transmission according to programmed instructions stored in the memory device in the control unit 138 or instructions supplied from the surface. Thus, the controller 138 (FIG. 1A) may be configured to operate autonomously downhole. A telemetry unit 139 (FIG. 1A) in the coring assembly 120 enables communication between the downhole devices and the surface via a link, such as a data and power bus (not shown), and establishes a two-way communication between the downhole devices and the surface controller 40. Any suitable telemetry system may be utilized for the purpose of this disclosure, including, but not limited to, a mud pulse telemetry system, an electromagnetic telemetry system, an acoustic telemetry system, and a wired pipe system. The wired-pipe telemetry system may include jointed drill pipe sections which are fitted with a data communication link, such as an electrical conductor or optical fiber. The data may also be wirelessly transmitted using electromagnetic transmitters and receivers across pipe joints or acoustic transmitters and receivers across pipe joints.

In embodiments, the barrel 132 functions as a container or storage volume for samples recovered from the formation. In one arrangement, the barrel 132 may be placed above the coring bit device 122 and the sealing member 130. The barrel 132 includes a first section 140 that receives the core 90 and a second section 142 that collects the gas that escapes from the core 90. The barrel 132 may utilize seals and other similar devices (not shown) to provide a liquid-tight or gas-tight environment for the first section 140 and/or the second section 142 to prevent the escaped gas from leaking out of the barrel 132 and/or to prevent degradation of the recovered samples. In embodiments, a movable piston 144 may be used to vary the volume of the barrel 132. In one arrangement or configuration, the barrel 132 may be formed as a removable or detachable component of the coring device 120. For instance, the barrel 132 may be an inner barrel that is received into a chamber of an outer barrel 136. The outer barrel 136 may be a housing that is formed in the coring device 120. In some embodiments, the inner barrel may be removed from the outer barrel at the surface. Additionally, in certain embodiments, a retrieval device 139 such as a wireline may be utilized to remove the inner barrel from the outer barrel while the coring device 120 is in the wellbore.

It should be understood that the terms first section and second section do not imply that these sections should be structurally separated. Rather, these terms generally refer to the volumes in a barrel wherein the core and the escaped gas reside. A barrel may have two regions or volumes that are formed within a single interior space. Alternatively, as described below, the two regions or volumes may be physically separated. It should also be understood that the barrel may be an assembly of components, not necessarily one integral body, and that the term "barrel" is not intended to imply a particular shape or construction. It may be a couple of chambers or containers suitable of performing the functions described herein.

Referring now to FIGS. 1A and 1B, during an exemplary deployment, the coring bit 122 drills into the formation to form the core 90. The core 90 travels through a bore 121 of the coring device 120 and passes through the sealing device 130. As noted previously, the sealing device 130 may be a ball valve that is initially set in an open position wherein a passage formed in the valve is aligned with the bore 131. After the core 90 clears the sealing device 130, the sealing device 130 is activated to seal off communication between the interior of the barrel 132 and the bore 121. The seal formed by the sealing device 130 may be a liquid-tight seal or a gas-tight seal. As the coring assembly 120 is retrieved to the surface, the decreasing wellbore pressure allows gas to escape from the core 90. As this gas collects in the second section 142, the movable piston 144 moves in the direction 146 to increase the volume available for the second section 142. The movable piston 144 may include seals 148 to form a gas-tight seal for the second section 142. In some embodiments, the second section 142 retains all of the gas escaping from the core 90, i.e., the total gas volume of the core. In other embodiments, the second section 142 retains only a portion of the gas escaping from the core 90. For instance, in some applications, the volume of escaping gas may initially be small and readily captured in the second section 142. However, as the second section 142 approaches the surface, the volume of escaping gas may be so large that a portion of the escaping gas may overflow and escape the second section 142. Thus, the second section 142 need not be perfectly sealed, but rather substantially sealed.

During the coring process and subsequent retrieval of the core 90 to the surface, one or more sensors 134 measure one or more parameters relating to the core 90, the escaping gas, and/or the environment in the barrel 132. These measurements may be made continuously or at specified intervals through autonomous operation of the downhole controller 138. In other arrangements, these measurements may be made on-demand from the surface. These measurements may be recorded to the downhole recorder and/or transmitted to the surface via the telemetry device 139. Additionally, these measurements can be also made and, if needed, recorded while the barrel 132 is at the surface. That is, for instance, the pressure and temperature of the core 90 and the escaped gas may be continuously monitored as the barrel 132 is transported to a facility for analysis. Other parameters and associated sensors will be discussed in greater detail later.

In a variant not shown, the piston 144 may be fixed to isolate the first section 140 from the second section 142. The piston 144 may include a valve, a permeable membrane, which may be reinforced to withstand a selected pressure differential, or other suitable flow control device that allows the escaped gas to flow from the first section 140 to the second section 142 during the retrieval process. In arrangements, the flow control device may be configured to regulate or modulate the flow rate of the escaped gas from the first section 140 to the second section 142. Control or throttling of the escaped gas flow may reduce the likelihood of fracturing of the core 90 due to a rapid outflow of gas from the core 90.

The barrel 132 is susceptible to numerous other embodiments, of which a few illustrative embodiments are described below. Referring now to FIG. 2, there is shown an embodiment wherein a barrel 150 includes a first section 152 for receiving a core 90 and a second section 154 for collecting a gas escaping from the core 90. As discussed previously, the barrel 132 and in particular the second section 142 is substantially-gas tight to prevent the escaped gas from leaking out of the barrel 150. Additionally, a pressure application device 156 may be used to control a pressure applied to the sample, i.e., the core 90 and escaped gas, in the barrel 150. The pressure application device 156 may be controlled to maintain a selected pressure or vary a pressure in the barrel 150. In embodiments, the pressure application device 156 may include a supply 158 of a pressurized fluid (e.g., gas or liquid), such as nitrogen, that is conveyed to a back side 162 of a movable piston 164. A flow control device 166, such as a valve, may be used to selectively flow the pressurized fluid to the barrel 150. In embodiments, the valve 166 may be operated by the controller 138 (FIG. 1A). This also allows the pressure of the second section to be relatively low at the surface for safe operations.

In one mode of operation, the core 90 is first deposited into the first section 152 in a manner previously described. Next, the valve 166 in response to a control signal transmitted by the controller 138 (FIG. 1A), conveys a pressurized fluid into the barrel 150. The movable piston 164 separates the pressurizing gas cushion from the core 90. During the retrieval process, the decreasing wellbore pressure allows gas to escape from the core 90. As this gas collects in the second section 154, the movable piston 164 moves in the direction 168 to increase the volume available for the second section 154. The pressurized fluid on the back side of the piston 164 applies a preset or predetermined pressure to the sample in the barrel 150. The preset pressure may be a formation pressure or other pressure value. As described previously, one or more parameters relating to the core 90, the escaped gas, and/or the barrel 150 may be measured by sensors 134 and recorded downhole and/or at the surface during this process.

Referring now to FIG. 3, there is shown yet another embodiment wherein a collection device 170 includes a first section 172 for receiving a core 90 and a second section 174 for collecting a gas escaping from the core 90. The first section 172 and the second section 174 may be physically separated as shown. Also, the first section 172 and the second section 174 may be components of one barrel. The second section 174 is substantially-gas tight to capture the escaped gas. In some embodiments, the second section 174 may be removable from the first section 172. A conduit 176 or flow line conveys gas escaping from the core 90 from the first section 172 to the second section 174. A flow control device 178, such as a valve, may be used to control flow along the conduit 176. In embodiments, the valve 178 may be operated by the controller 138 (FIG. 1A). In one mode of operation, the core 90 is first deposited into the first section 172 in a manner previously described. Next, the valve 178 in response to a control signal transmitted by the controller 138, allows fluid communication between the first second 172 and the second section 174. During the retrieval process, the decreasing wellbore pressure allows gas to escape from the core 90 and collect in the second section 174 via the conduit 176. In arrangements, the valve 178 may be controlled to modulate the flow rate of the escaped gas from the first section 172 to the second section 174. Additionally, a pressure application device as discussed previously may be used to apply pressure to the sample, i.e., the core 90 and escaped gas, in the first section 172 and/or the second section 174.

At the surface, the second section 174 may be disconnected from the collection device 170 and transported to a suitable facility. Thus, in embodiments, the second section 174 may be a department of transportation approved sample collection tank. Also, the first section 172 may also be formed as a pressurized container. Additionally, in embodiments, the second section 174 may include a sampling port 182 from which a sample of the escaped gas may be retrieved. The sampling port 182 may also be formed as a window that is transparent to optical waves or other types of energy waves. Any suitable spectrometer may be utilized for analyzing the gas in the second section 174 for obtaining information about the core or the formation. As described previously, one or more parameters relating to the core 90, the escaped gas, and/or the sections 172/174 may be measured by the sensors 134 and recorded downhole and/or at the surface during this process.

Referring now to FIG. 1B, as discussed previously, the coring assembly 120 may include a variety of sensors and devices, generally designated by numeral 134, for taking measurements relating to one or more properties or characteristics of the: (i) core 90; (ii) the gas that has escaped from the core 90; and (iii) the environment or conditions within the barrel 120. In one embodiment, the sensors measure or estimate parameters that may be used to estimate a gas saturation of a formation. By gas saturation, it is generally meant the volume of gas within a specified region of the formation or a gas storage capacity of a formation. The total amount of released gas from a sample may be determined by using the molecular mass of the escaped gas, a reservoir temperature, volume of core sample, and its initial and final pressures. In general, a gas law may be utilized to determined the volume of released or escaped gas:

$$pV = ZnRT$$

$$n = m/M$$

where p is pressure, V is volume, Z denotes the deviation factor of the real gas, R is gas constant, T represents the temperature, M is molecular mass of gas, m is the gas mass, and n is the mole number. Thus, to evaluate gas saturation of the formation, the coring device 120 may include sensors 134, such as a pressure sensor and a temperature sensor, that provide data that may be inputted into the mathematical algorithms or models that estimate gas saturation. Additionally, the coring device 120 may include an acoustic sensor or other suitable device to measure the gas volume inside the section in which the gas is contained. This measurement may be used to determine the volume of the escaping gas and/or may be used to evaluate the accuracy of an analytically determined volume of the escaping gas.

In one method, determining a desired formation parameter or characteristic, such as gas saturation, may be performed at the surface. In such a method, parameters such as pressure and temperature may be measured at the time the sample is cut from the formation and also measured continuously or at specified intervals as the sample is retrieved to the surface. These measurements may be recorded downhole and/or transmitted via the telemetry device 139 to the surface and recorded by surface equipment. Once at the surface, the sample may be subjected to further analysis that may be used to define values for a mathematical model based on the gas law or other suitable model. Thereafter, suitable mathematical models may be utilized in conjunction with the measured data and any other data obtained through surface analysis to estimate the desired parameter or property.

It should be appreciated that exemplary methods according to the present disclosure may also utilize transient measurements at one or more selected depths in the wellbore to estimate properties or characteristics such as permeability, porosity, and gas saturation. The transient measurements may be taken at any selected depth.

In one exemplary method utilizing transient measurements, downhole measurements of one or more selected parameters relating to the escaping gas may be utilized to determine permeability and porosity. In an illustrative method, parameters indicative of permeability and porosity may be measured and recorded at discrete time intervals (e.g., every 0.10 seconds, every 1 second, every 5 minutes, etc.) at one or more selected depths as the sample is retrieved to the surface. These values, as well as the rate of change of these values over time, may be used to estimate one or more properties or characteristics of the formation. For instance, a core being retrieved from a formation may be stationary at one or more depths for a period of time that may range from a few seconds to a few minutes or more. During one or more of these stationary periods, sensors may measure the pressure and the temperature in the barrel of the coring device. At generally the same time and depth, a sensor may measure the volume of the escaped gas. Because these measurements are taken at selected time intervals, a data set of these parameters versus time is generated. This data may be recorded downhole and/or at the surface. Thereafter, these data sets from one or more selected depths and known mathematical models may be used to estimate a permeability and/or porosity of the core sample.

Another illustrative method for determining a gas volume may include determining an accumulative flow rate of free gas at discrete or selected depths. Again, utilizing downhole measurements of selected parameters such as pressure, temperature and volume, a flow rate may be determined at each of the selected depths. Using known integration techniques, the total volume of gas that has escaped from the core may be determined using these determined flow rates.

In another method, the determination of gas saturation may be performed entirely downhole using an appropriately programmed downhole controller and data obtained by the sensors 134. To obtain information such as chemical composition that may be used as inputs into the mathematical models described previously, a suite of sensors and devices may be utilized to analyze the core 90 and the escaped gas. Illustrative sensors include, but are not limited to, an acoustic sensor for measuring one or more acoustic properties or other properties of the core 90; a nuclear magnetic resonance ("NMR") device for estimating permeability and other rock properties of the core 90; sensors to estimate pore saturation, pore pressure, wettability, internal structure of the core 90; optical devices, including spectrometers, for determining fluid properties and/or fluid composition (such as proportions of oil, gas, water, mud contamination, etc.), absorbance, refractive index, and presence of certain chemicals; laser devices; nuclear devices; x-ray devices, etc. The sensors 90 may also include nuclear sensors (neutron and chemical source based sensors), pressure sensors, temperature sensors, gamma ray and x-ray sensors. In such a method, the downhole controller 138 may utilize these measurements and suitable mathematical models to estimate the desired parameter or property. Alternatively or additionally, the downhole controller 138 may be preprogrammed with estimated or assumed values of one or more inputs of those mathematical models.

From the above, therefore, it should be appreciated that what has been described includes an apparatus for recovering cores cut from a subterranean formation as well as gas escaping from such cores. In embodiments, the apparatus may include a barrel having two sections: one section for receiving the core and another section for collecting gas escaping from the core. The sections may be volumes in one interior space or structurally separated volumes. The apparatus may include one or more sensors to provide signals relating to a property of interest relating to the escaping gas. The pressure in either or both of the sections may be controlled. Also, the second section may be removable from the first section and may also be substantially gas tight. Illustrative sensors include a pressure sensor, a temperature sensor, and sensor to estimate the gas volume, such as an acoustic sensor. The apparatus may also include a recorder that records data representative of the signals received from the sensor(s). The recorder may record data as the barrel is retrieved from a selected depth in the wellbore to a surface location.

From the above, it should also be appreciated that what has been described includes a method for estimating a parameter of interest relating to a formation. The method may include retrieving a core from the formation; collecting a gas escaping from the core as the core is retrieved to the surface; and measuring at least one parameter of interest relating to the escaping gas while the core is retrieved to the surface. The method may also include controlling a pressure applied to either or both of the core and the gas escaping from the core. The method may include containing the escaped gas in a container that is removable or detachable from the container for the core. In aspects, the parameters of interest that are measured include pressure, temperature, and a volume occupied by the escaping gas. The method may further include measuring the parameters as the escaped gas and core are retrieved to the surface. These parameters may be measured for a selected period of time at one or more depths to determine transient gas flow out of the core. The method may also include estimating gas saturation, a permeability, and/or porosity of a formation using one or more of the measured parameters.

While the foregoing disclosure is directed to certain embodiments that may include certain specific elements, such embodiments and elements are shown as examples and various modifications thereto apparent to those skilled in the art may be made without departing from the concepts described and claimed herein. It is intended that all variations within the scope of the appended claims be embraced by the foregoing disclosure.

The invention claimed is:

1. An apparatus for use in a wellbore, comprising:
    a tool having a first section configured to receive a core and a second section configured to collect a gas escaping from the core; and
    a sensor configured to provide signals representative of a property of interest relating to the collected gas during retrieval of the tool from the wellbore.

2. The apparatus of claim 1 further comprising a device configured to pressurize the second section.

3. The apparatus of claim 1 wherein the second section is removable from the first section.

4. The apparatus of claim 1 wherein the second section is substantially gas tight.

5. The apparatus of claim 1 wherein the sensor is one of: a pressure sensor, a temperature sensor, and a sensor to estimate gas volume.

6. The apparatus of claim 1 wherein the second section includes an optical window.

7. The apparatus of claim 1 further comprising a recorder configured to record data representative of the signals received from the sensor.

8. The apparatus of claim 7 wherein the recorder is configured to record data as the core is retrieved from a selected depth in the wellbore to a surface location.

9. The apparatus of claim 1 further comprising a processor configured to receive data from the sensor and provide an estimate of a property of interest of a formation.

10. The apparatus of claim 9 wherein the property of interest of the formation is one of: gas saturation of the formation; permeability of the formation; and porosity of the formation.

11. A method for estimating a parameter of interest of a formation, comprising:
    conveying a tool into a wellbore surrounding the formation;
    retrieving a core from the formation using the tool into a first section;
    collecting a gas escaping from the core into a second section; and
    measuring a property of the collected gas during retrieval of the tool from the wellbore using a sensor.

12. The method of claim 11 further comprising pressurizing the second section.

13. The method of claim 11 wherein the property is one of: pressure, temperature, and gas volume.

14. The method of claim 11 further comprising estimating a property of the formation using the property of the collected gas, wherein the property of the formation is one of: permeability, porosity and gas saturation.

15. The method of claim 11 further comprising recording measurements from the sensor while retrieving the tool from the wellbore.

16. The method of claim 11 wherein the second section includes an optical window and the method further comprises performing a spectroscopic analysis of the collected gas in the second section.

17. The method of claim 11 wherein the second section is removable.

18. The method of claim 11 further comprising taking measurements of pressure, temperature and gas volume in the second chamber at a plurality of depths during retrieval of the tool from the wellbore and determining a property of the formation using such measurements and a math model.

19. A method for estimating a parameter of interest of a formation, comprising:
    conveying a tool into a wellbore surrounding the formation;
    retrieving a core from the formation using the tool into a first section;
    collecting a gas escaping from the core into a second section;
    taking measurements of a plurality of properties of the collected gas in the second chamber during retrieval of the tool from the wellbore;
    recording the taken measurements of the plurality of measurements; and
    estimating the property of interest of the formation using the recorded measurements.

20. The method of claim 19 further comprising processing the recorded measurement to estimate the property of interest of the formation as one of: during retrieval of the tool from the wellbore; using a processor in the downhole tool; or using a processor at the surface.

* * * * *